(12) United States Patent
Bertrand et al.

(10) Patent No.: US 6,736,769 B2
(45) Date of Patent: May 18, 2004

(54) RADIOACTIVITY LOCAL DELIVERY SYSTEM

(76) Inventors: Olivier Bertrand, 7505 de Dieppe Street, Montreal Quebec (CA), H3R 2T9; Rosaire Mongrain, 7462 de la Malicome Avenue, Anjou Quebec (CA), H1M 2W9

( * ) Notice: Subject to any disclaimer, the term of this patent is extended or adjusted under 35 U.S.C. 154(b) by 0 days.

(21) Appl. No.: 09/851,801

(22) Filed: May 9, 2001

(65) Prior Publication Data

US 2002/0090338 A1 Jul. 11, 2002

Related U.S. Application Data

(63) Continuation of application No. 09/171,384, filed as application No. PCT/CA97/00262 on Apr. 17, 1997, now abandoned.
(60) Provisional application No. 60/015,788, filed on Apr. 17, 1996.

(51) Int. Cl.[7] .............................................. A61N 5/00
(52) U.S. Cl. ......................................................... 600/1
(58) Field of Search ................................. 600/300, 481, 600/1–8, 500, 504; 128/897, 898; 424/1.11

(56) References Cited

U.S. PATENT DOCUMENTS

| | | |
|---|---|---|
| 4,707,352 A | 11/1987 | Stavrianopoulos |
| 5,059,166 A | 10/1991 | Fischell et al. |
| 5,176,617 A | 1/1993 | Fischell et al. |
| 5,199,939 A | 4/1993 | Dake et al. |
| 5,354,257 A | 10/1994 | Roubin et al. |
| 5,364,612 A | 11/1994 | Goldenberg |
| 5,383,928 A | 1/1995 | Scott et al. |
| 5,411,466 A | 5/1995 | Hess |
| 5,464,450 A | 11/1995 | Buscemi et al. |
| 5,571,713 A | 11/1996 | Lyle et al. |
| 5,688,486 A | 11/1997 | Watson et al. |
| 5,919,126 A * | 7/1999 | Armini .......................... 600/3 |
| 5,942,209 A | 8/1999 | Leavitt et al. |
| 6,152,869 A * | 11/2000 | Park et al. ....................... 600/3 |
| 6,192,095 B1 * | 2/2001 | Sekine et al. ................ 376/189 |
| 6,261,320 B1 * | 7/2001 | Tam et al. .................. 623/1.15 |

FOREIGN PATENT DOCUMENTS

| | | |
|---|---|---|
| DE | 43 13 002 | 8/1994 |
| EP | 433 011 | 6/1992 |
| WO | WO 95/09659 | 4/1995 |
| WO | WO 95/19167 | 7/1995 |

OTHER PUBLICATIONS

Serruys et al.; "A Comparison of Balloon–Expandable–stent Implantation with Balloon Angioplasty in Patients with Coronary Artery Disease"; *New England Journal of Medicine*; vol. 331, No. 8, pp. 489–495, Aug. 25, 1994.

(List continued on next page.)

*Primary Examiner*—Samuel G. Gilbert
(74) *Attorney, Agent, or Firm*—Merchant & Gould P.C.

(57) ABSTRACT

To determine a coefficient of diffusion of a radioisotope in a radioisotope-containing implant structure and to calculate a quantity of radioisotope to be introduced in an implant structure in view of administering to a vascular region of a patient's body a dose of radioactivity at a given dose rate, a relation is calculated between a coefficient of diffusion of the radioisotope in the implant structure and a coefficient of diffusion of the radioisotope in the vascular region of the patient's body for at least one given period of time during which the radioisotope has to be released. The diffusion coefficient of the vascular region is determined. The method also determines, from the diffusion coefficient of the vascular region and in connection with the above relation, the diffusion coefficient of the implant structure required to release the radioisotope within the given period of time. Finally, the quantity of radioisotope is calculated from the diffusion coefficient of the vascular region and the diffusion coefficient of the implant structure. The implant structure may comprise a helical stent with a polymer coating incorporating the radioisotope and with struts with varying spacing.

12 Claims, 7 Drawing Sheets

OTHER PUBLICATIONS

Schwartz et al.; "Proliferation Analysis of Arterial Neointimal Hyperplasia: Lessons for Antiproliferative Restennosis Therapies"; *International Journal of Cardiology 53*; 1996; pp. 71–80.

Fischman et al.; "A Randomized Comparison Of Coronary–Stent Placement And Balloon Angioplasty In The Treatment Of Coronary Artery Disease"; *The New England Journal of Medicine*; Aug. 25, 1994; pp. 496–501.

Cross et al.; "A Short Atlas of Beta–Ray Spectra"; *Phys. Med. Biol.*; vol. 28, No. 11, pp. 1251–1260; 1983.

Fischell et al.; "B–Particle Emission from Stent Wire"; *Circulation*; vol. 92, No. 5, pp. 1353–1354; Sep. 1, 1995.

Weintraub et al.; "Can Restenosis after Coronary Angioplasty be Predicted from Clinical Variables?"; *Journal of American College of Cardiology*; vol. 21, No. 1, pp. 6–14; Jan. 1993.

Popma et al.; "Clinical Trials of Restenosis after Coronary Angioplasty"; *Circulation*; vol. 84, No. 3, pp. 1426–1436; Sep. 1991.

K.A. Connors; "Complex Formation"; Chapter 14, pp. 169–182.

Karas et al.; "Coronary Intimal Proliferation after Balloon Injury and Stenting in Swing: An Animal Model of Restenosis"; *Journal of American College of Cardiology*; vol. 20, No. 2, pp. 467–474; Aug. 1992.

Kakuta et al.; "Differences in Compensatory vessel enlargement, not intimal formation, account for restenosis after angioplasty in the hypercholesterolemic rabbit motel"; *Circulation*; vol. 89, No. 6, pp. 2809–2815; Jun. 1994.

Schwartz et al.; "Differential neointimal response to coronary artery injury in pigs and dogs"; *Arteriosclerosis and Thrombosis*; vol. 14, No. 3, pp. 395–400; Mar. 1994.

Remington: The Science and Practice of Pharmacy (see Chapter 14. pp. 169–182), 1995.

Lincoff et al.; "Local Drug Delivery for the prevention of restenosis: Fact, Fancy and future"; *Circulation*; Vo. 90, No. 4, pp. 2070–2081; Oct. 1994.

Johnson et al.; "Review of radiation safety in the cardiac catheterization laboratory"; *Catheterization and Cardiovascular Diagnosis*; Wiley–Liss Inc.; pp. 186–194.

Hunink et al.; "Risks and benefits of femoropopliteal percutaneous balloon angioplasty"; *Journal of Vascular Surgery*; vol. 17, No. 2, pp. 183–194; Jan. 1993.

Dutreix; "Role du Debit de Dose en Curietherapie"; *I. Bases techniques et dosimetriques*; pp. 71–84.

Hall et al.; "The dose–rate effect revisited: Radiobiological considerations of importance in radiotherapy"; *International Journal of Radiation Oncology, Biology and Physics*; vol. 21, No. 6, pp. 1403–1414; Nov. 1991.

Byhardt et al.; "The Heart and Blood Vessels"; *Radiation Oncology; Rationale, Technique, Results*; Chapter 13; pp. 277–284.

Steve Webb; "The Physics of Medical Imaging"; *Institute of physics publishing, bristol and philadelphia*; p. 261.

Brenner et al.; "The radiobiology of intravascular irradiation"; *Int. J. Radiation Oncology Biol. Phys.*; vol. 36, No. 4, pp. 805–810; 1996.

Fager; "Thrombin and proliferation of vascular smooth muscle cells"; *Circulation Research*; vol. 77, No. 4, pp. 645–650; Oct. 1995.

Condado et al.; "Tolerance of intracoronary radiation therapy (ICRT) after percutaneous revascularization procedures (PRP)"; *1st International Meeting on Interventional Cardiology*; vol. 7, Supple. C, pp. 25C; 1995.

March et al.; "8–Methoxypsoralen and Longwave ultraviolet irradiation are a novel antiproliferative combination for vascular smooth muscle"; *Circulation*; vol. 87, No. 1, pp. 184–191; Jan. 1993.

"Discoveries in Radiation for Restenosis"; Atlanta, Georgia; Abstracts 1–44; pp. 1–142; Jan. 11–12, 1996.

Schwartz et al.; "Effect of external beam irradiation on neointimal hyperplasia after experimental coronary artery injury"; *Journal of American College of Cardiology*; vol. 19, No. 5, pp. 1106–1113; Apr. 1992.

Carter et al.; "Effects of endovascular radiation from a B–particle–emitting stent in a porcine coronary restenosis model: A dose–response study"; *Circulation*; vol. 94, No. 10, pp. 2364–2368; Nov. 15, 1996.

Wiedermann et al.; "Effects of high–dose intracoronary irradiation on vasomotor function and smooth muscle histopatholoty"; *Intracoronary irradiation and vasomotion, American College of Cardiology*; H125–H132; 1994.

Waksman et al.; "Endovascular low–dose–irradiation inhibits neointima formation after coronary artery balloon injury in swine: a possible role for radiation therapy in restenosis prevention"; *Circulation*; vol. 91, No. 5, pp. 1533–1539; Mar. 1, 1995.

Bottcher et al., "Endovascular irradiation–a new method to avoid recurrent stenosis after stent implantation in peripheral arteries: technique and preliminary results", *International Journal of Radiation Oncology, Biology and Physics*; vol. 29, No. 1, pp. 183–186; 1994.

Waksman et al.; "Endovascular radiation prior to stent implantation inhibits neointimal proliferation in porcine coronary arteries"; Abstract No. 773–1; 187A; Mar. 22, 1995.

Verin et al.; "Feasibility of intracoronary B–irradiation to reduce restenosis after balloon angioplasty: A Clinical pilot study"; *circulation*; vol. 95, No. 5, pp. 1138–1144; Mar. 4, 1997.

Shimotakahara et al.; "Gamma irradiation inhibits neointimal hyperplasia in rats after arterial injury"; *Stroke*; vol. 25, No. 2, pp. 424–428; Feb. 1994.

Kuntz et al.; "Generalized model of restenosis after conventional balloon angioplasty, stenting and directional atherectomy"; *Journal of American College of Cardiology*; vol. 21, No. 1, pp. 15–25; Jan. 1993.

Laird et al.; "Inhibition of neointimal proliferation with a beta particle emitting stent"; Abstract No. 773–3; 287A; Mar. 22, 1995.

Laird et al.; "Inhibition of neointimal proliferation with low–dose irradiation from a B–Particle–emitting stent"; *Circulation*; vol. 93, No. 3, pp. 529–536; Feb. 1, 1996.

Bergonie et al., "Interpretation of some results of radiotherapy and an attempt at determining a logical technique of treatment"; *Radiation Research 11*; pp. 587–588; 1959.

Verin et al.; "Intra–arterial beta irradiation prevents neointimal hyperplasia in a hypercholesterolemic rabbit restenosis model"; *Circulation*; vol. 92, No. 8, pp. 2284–2290; Oct. 15, 1995.

Serruys et al.; "Intracoronary brachytherapy: The death knell of restenosis or just another episode of a never–ending story?"; *Circulations*; vol. 96, No. 3, pp. 709–711; Aug. 5, 1997.

Wiedermann et al.; "Intracoronary irradiation markedly reduces neointimal proliferation after balloon angioplasty in swine: persistent benefit at 6–month follow–up"; *Journal of the American College of Cardiology*; vol. 25, No. 6, pp. 1451–1456; May 1995.

Wiedermann et al.; "Intracoronary irradiation markedly reduces restenosis after balloon angioplasty in a porcine model"; *Journal of American College of Cardiology*; vol. 23, No. 6, pp. 1491–1498; May 1994.

Waksman et al.; "Intracoronary low–dose b–irradiation inhibits neointima formation after coronary artery baloon injury in the swine restenosis model"; *Circulation*; vol. 92, No. 10, pp. 3025–3031; Nov. 15, 1995.

Waksman et al.; "Intracoronary radiation before stent implantation inhibits neointima formation in stented porcine coronary arteries"; *Circulation*; vol. 92, No. 6, pp. 1383–1386; Sep. 15, 1995.

Amon et al.; "Introduction of a new coronary stent with enhanced radioopacity and hemocompatibility"; *IEEE*; 1995.

"Local Drug Delivery for thrombosis and restenosis"; Abstracts No. 891 (891–26, 891–27 891–28 and 891–29) of JACC; 186A; Feb. 1994.

Condado et al.; "Long–term angiographic and clinical outcome after percutaneous transluminal coronary angioplasty and intracoronary radiation therapy in humans"; *Circulation*; vol. 96, No. 3, pp. 727–732; Aug. 5, 1997.

Waksman et al.; "Long–term efficacy and safety of endovascular low dose irradiation in a swine model of restenosis after angioplasty"; Abstract No. 773–4; 287A; Mar. 22, 1995.

Fischell et al.; "Low–dose, B–particle emission from "stent" wire results in complete localized inhibition of smooth muscle cell proliferation"; *Circulation*; vol. 90, No. 6, pp. 2956–2965; Dec. 1994.

Hehrlein et al.; Low–dose radioactive endovascular stents prevent smooth muscle cell prliferation and neointimal hyperplasia in rabbits; *Circulation*; vol. 92, No. 6, pp. 1570–1575; Sep. 15, 1995.

Soares et al.; "Measurement of radial dose distributions around small beta particle emitters using high resolution radiochromic foil dosimetry"; *Nuclear Technology Publishing*; vol. 47, No. 121, pp. 367–372; 1993.

Condado et al.; "Late follow–up after percutaneous transluminal coronary angioplasty (PTCA) and intracoronary radiation therapy (ICRT)"; Abstract 34.

Katzen et al.; "Mechanical approaches to restenosis in the peripheral circulation"; Miami Vascular Institue at Baptist Hospital.

Condado et al.; "Percutaneous transluminal angioplasty (PTCA) and intracoronary radiation therapy (ICRT): a possible new modality for the treatment of coronary retensosis: a preliminary report of the first 10 patients treated with intracoronary radiation therapy"; Abstract No. 773–6 of JJCA; Feb. 1995.

Dorros et al.; "Percutaneous transluminal coronary angioplasty: report of complications from the national heart, lung, and blood institute PTCA registry"; *Circulation*; vol. 67, No. 4, pp. 723–729; Apr. 1983.

Hafeli et al.; "Polymeric radiopharmaceutical delivery systems"; *Radioactivity & Radiochemistry*; vol. 3, No. 4, pp. 11–14; Nov. 4, 1992.

Wagner et al.; "Potential biological effects following high x–ray dose interventional procedures"; *Journal of Vascular and Interventional Radiology*; pp. 71–84; Jan.–Feb. 1994.

Liermann et al.; "Prophylactic endovascular radiotherapy to prevent intimal hyperplasia after stent implantation in femoropopliteal arteries"; *Cardiovasc Intervent Radiol.*; pp. 12–16; 1994.

Fowler et al.; "Pulsed brachytherapy: The conditions for no significant loss of therapeutic ratio compared with traditional low dose rate brachytherapy"; *Int. J. Radiation Oncology Biol. Phys.*; vol. 23, No. 3, pp. 661–669; 1992.

Hehrlein et al.; "Pure B–particle–emitting stents inhibit neointima formation in rabbits"; *Circulation*; vol. 93, No. 4, pp. 641–645; Feb. 15, 1996.

Haude et al.; "Quantitative analysis of elastic recoil after balloon angioplasty and after intracoronary implantation of balloon–expandable palmaz–schatz stents"; *Journal of American College of Cardiology*; vol. 21, No. 1, pp. 26–34; Jan. 1993.

Unterberg et al.; "Reduced acute thrombus formation results in decreased neointimal proliferation after coronary angioplasty"; *Journal of American College of Cardiology*; vol. 26, No. 7, pp. 1747, 1749, 1751; 1754; Dec. 1995.

Hamon et al.; "Restenosis after coronary angioplasty"; European Heart Journal ; Supplement 1; pp. 33–48; 1995.

Schwartz et al.; "Restenosis after balloon angioplasty: A Practical proliferative model in porcine coronary arteries"; *Circulation*; vol. 82, No. 6, pp. 2190–2199; Dec. 1990.

Buerk, D. et al., "Spatial Variation of Aortic Wall Oxygen Diffusion Coefficient from Transient Polarographic Measurements," *Ann. Biomed. Eng.*, vol. 20, pp. 629–646 (1992).

Glatz, C. et al., "Influence of Glycosaminoglycan Content on Mass Transfer Behavior of Porcine Artery Wall," *Atheroscelrosis*, vol. 25, pp. 153–163 (1976).

Lovich, M. et al., "Computational Simulations of Local Vascular Heparin Deposition and Distribution," *Am. J. Physiol.*, vol. 271, pp. H2014–H2024 (1996).

* cited by examiner

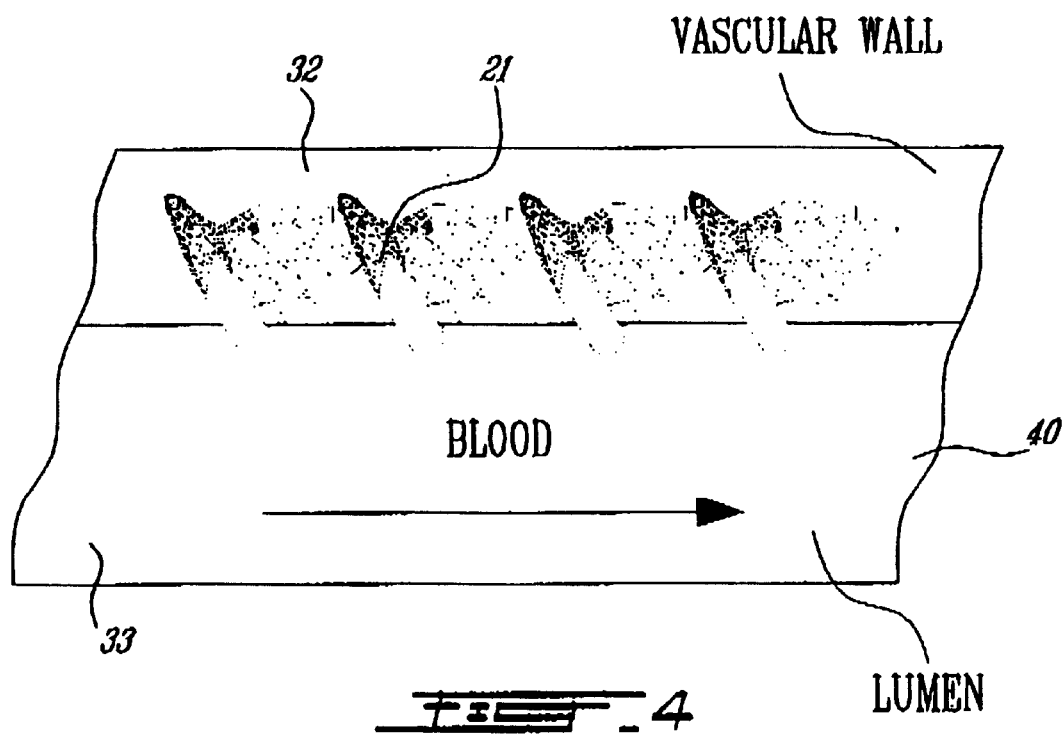
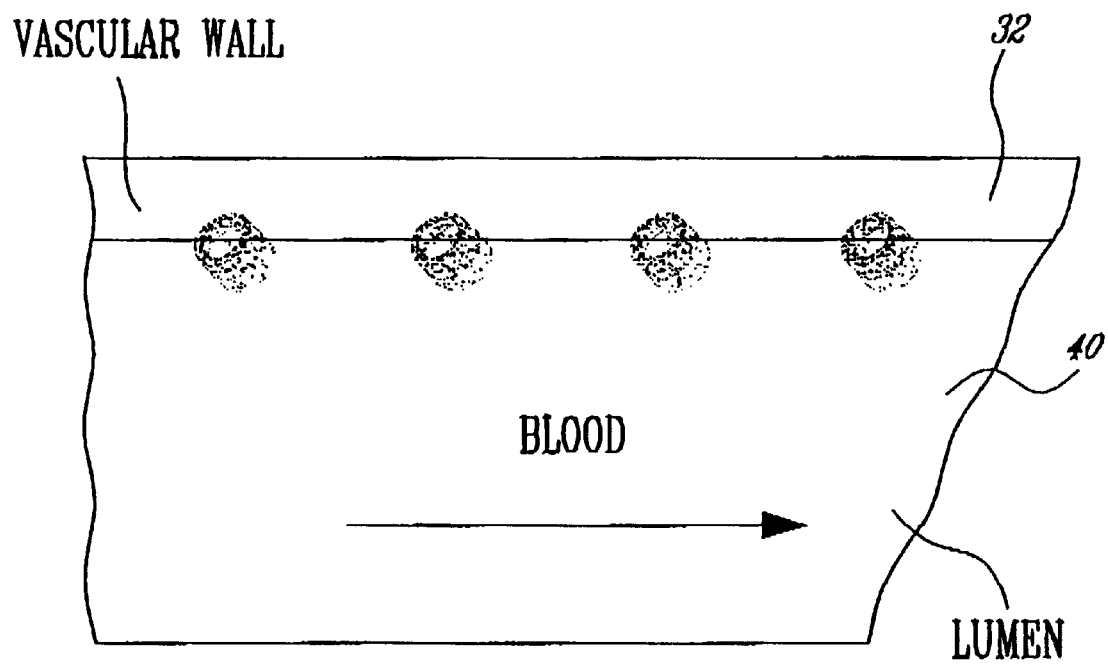

RADIOACTIVITY LOCAL DELIVERY SYSTEM

This application is a continuation-in-part application of Ser. No. 09/171,384, filed Feb. 16, 1999, now abandoned which is a National Phase application of PCT/CA97/00262 filed April 17, 1997 which is the International application of U.S. Provisional application Serial No. 60/015,788 filed Apr. 17, 1996

BACKGROUND OF THE INVENTION

1. Field of the Invention

The present invention relates to local delivery of radioactivity. The present invention also relates to localized inhibition of cell proliferation using radioactivity.

2. Brief Description of the Prior Art

The therapeutic use of radiation therapy to reduce the proliferation of rapidly dividing cells has evolved from the Bergonié and Tribondeau Law of radiobiology which states that proliferative cells are more radiosensitive than normal cells (Bergonié and Tribondeau, 1959, Radiat. Res. 11:587). Hence, radiation therapy can be used to reduce proliferation cells in a tumor. The Bergonié and Tribondeau principle needs not be limited to the treatment of malignant tumors, however. A number of clinical situations require the reduction of cell proliferation: treatment of heterotopic bone formation, prevention of cheloids and more recently the inhibition of intimal hyperplasia. Having discovered that smooth muscle cell proliferation is inhibited after irradiation, radiation therapy has thus been applied to reduce the restenosis process following coronary angioplasty.

Coronary angioplasty is actually a well-established technique for the treatment of obstructive coronary disease. More than 500,000 angioplasties are performed every year worldwide. However, two major problems remain unsolved.

The first problem is acute closure, reported to occur in up to 11% of the cases after balloon angioplasty (Dorros et al., 1983, Circulation 67:723–730). In that context, intracoronary stenting appears as an invaluable procedure for the treatment of extensive dissections occurring after angioplasty. As a scaffolding vessel wall support, it preserves adequate coronary opening and perfusion.

The second problem is restenosis which has been shown to occur in 30 to 50% of the cases. So far, drug therapy has shown limited results in reducing the extent of the phenomenon (Popma J J et al., 1991, Circulation 84:1426–1436). Intracoronary stents have been shown in randomized trials, to reduce restenosis from 42% to 32% in the Stress trial while from 32% to 22% in the Benestent trial (Fischman D L. et al., 1994, N. Engl. J. Med. 331:496–501; Serryus P W. et al., 1994, N. Engl. J. Med. 331:489–495). The beneficial effect of stenting is presumably due to a better vessel geometry after dilation, although stenting has been proved to induce more neo-intima formation than other devices in swine (Karas S P. et al., 1992, J. Am. Coll. Cardiol. 20:467–474). Indeed, swine has been recognized as a relevant animal model for restenosis although the rat and rabbit animal models are also widely used. Morphologically and hemodynamically the porcine coronary vascular system is very similar to the human coronary system. Reproducible intimal proliferation is obtained after balloon injury in the pig coronary arteries. Histologically, the proliferative response to balloon injury in the pig coronary is very similar to the response seen in pathological studies of humans (Schwartz et al., 1990, Circulation 82:2190–2200).

Balloon dilation leads to global vascular lesions which include mechanical deformation of the vessel, extensive destruction of the endothelium and immediate formation of thrombus. All of these act through vasoactive hormones, growth factors, circulating cells and presumably lipids on the media muscle cells. It is observed that smooth muscle cells are activated and migrate to the intima where after proliferation and matrix secretion, a "neo-intima" is generated [Hamon et al., 1995, Eur Heart J 16(*Suppl* 1):33–48]. This observation led to the proposal of a cellular mechanism for restenosis (FIG. 1). The role of elastic recoil and vessel remodeling has also been recognized following angioplasty (Kakuta T. et al., 1994, Circulation 89:2809–2815). Finally, thrombus adhesion through growth factors liberation, also plays a major role in the activation cascade (Fager G. et al., 1995, Circ. Res. 77:645–650).

Until now, drug therapy has consistently been focused on proliferation and thrombus inhibitions (Popma J J et al., 1991, Ibid.). Unfortunately, no significant effects were observed in human coronary restenosis when the drugs were administered systemically (Popma J J et al., 1991, Ibid.). The lack of a sufficient local drug concentration is the most common advocated reason to explain the inability to reduce neointima formation in humans. The research has thus targeted the local delivery of different drugs to prevent restenosis (Lincoff A M et al., 1994, Circulation 90(4):2070–2084). New catheters are already available to deliver drugs locally after angioplasty and feasibility trials are being conducted (Fram D B et al., 1994, J. AM. Coll. Cardiol. 23:186A).

Although the genetic and molecular understanding of the different mechanisms involved in restenosis have also been greatly improved, due to its complexity, the clinical genetic treatment of restenosis is expected to be very expensive and not readily available for still some time (Bennet M R. et al., 1995, Circulation 92:1981–1993).

The use of radiotherapy to reduce neointima formation was thus identified as a possible solution to the restenosis problem. Three basic approaches utilizing radiotherapy have thus been proposed:

1) External Irradiation:

External delivery using Gamma or Beta irradiation, showed that, at the single high dose used, a decrease in hyperplasia is observed. However, some groups detected fibrosis or necrosis in the irradiated region (Schwartz R S. et al., 1992, J. Am. Coll. Cardiol. 19:1106–1113). Moreover, this type of approach encompasses the irradiation of a large field.

2) Radioactive Catheter:

Experiments carried out with endovascular irradiation at the high dose/rate of Beta or Gamma rays produced a significant reduction in neointimal formation. However, this positive effect seems to be accompanied by fibrosis of the vessel resulting in a loss of vascular function thereof, suggesting that in the long term such a type of treatment might be detrimental. Furthermore, the irradiation treatment at the time when peak proliferation potential of the smooth muscle cells occurs (i.e. 24–48 hours) would be at best impractical in a clinical situation. Moreover, arteries receiving higher doses showed an increase diameter suggesting that irradiation would affect vessel remodeling [Waksman R. et al., 1995, J. A. Coll. Cardiol. (Special Issue (February 95)]. Of note, Brenner et al., 1996 (Radiation Oncology Biol. Phys. 36: 805–809) showed that a single high dose does not inhibit restenosis. Also, it has been reported that a 18 Gy single irradiation, failed to show a significant reduction in restenosis.

2) Radioactive Stents:

The group of Fischell studied the effects of $P^{32}$ stent wire on smooth muscle cells and endothelial cells proliferation in tissue culture (Fischell T A. et al., 1994, Circulation 90: 2956–2963; and U.S. Pat. No. 5,059,166 and 5,176,617). Titanium wire which was first impregnated with $P^{31}$ and then activated in a fission reactor was used. The resulting radioactive stent is thought to be emitting Beta radiation, although contaminating a and y emissions are likely because of the impregnation method. The use of such a stent on muscle cells demonstrated a dose response curve of inhibition at linear activities. However, at the highest wire activity level, there was inhibition observed as far as 10.6 mm from the wire.

This degree of penetration suggests that the stent emitted Gamma rays and that the use thereof in vivo would not deliver the radiation specifically to the targeted site, since a significant amount of normal surrounding tissue would be irradiated. This issue, amongst others, was indeed raised by Crocker et al., 1995 (Circulation 92:1353). The ion implantation technique creates lattice defects in the metallic crystal structure resulting in stoichiometric modification. These defects can contribute to diffusion of ions (leeching) modification of surface potential and alterations in clinical properties. Consequently, this method of radioactivation can alter the biocompatibility of the stent surface and hamper human clinical use.

Radiotherapeutic treatments using radioactive stents showed a significant dose-dependent reduction in neointima formation; this suggested a delayed regeneration of endothelial cells. Together with the long-range irradiation of surrounding tissues, this type of stent can be foreseen as having detrimental effects, especially in the long term, on the integrity and functionality of the treated vessel and surrounding tissues.

As mentioned previously, a number of animal models have been used to assess the feasibility and elaborate the methods of radiation therapy to be applied to humans. Radiotherapy of cancer is currently routinely used in humans. However, local delivery of radioactivity has yet to show its full potential. Only a few studies on radiation therapy following angioplasty in humans have been performed. All experiments dealt with relatively high dose rates. Using $Ir^{192}$ Gamma irradiation source which delivered 2000 cGy in durations lasting from 5 to 15 min [Condado J A. et al., 1995, J. Inv. Cardiol., 1995, 7(SupplC):25C; Condado J A. et al., 1995, J. AM. Coll. Cardiol., 1995, (*Special Issue* (February 95):288A], mild spasms occurred in the majority of the treated coronary arteries. However, with the group which received 2500 cGy, 7 out of 8 treated arteries developed aneurisms. In the group with 2000 cGy, out of 12 treated arteries 4 developed restenosis. Thus, side effects with significant potential health hazard were recorded.

The feasibility of radiation therapy to inhibit cellular proliferation is suggested by increasing data on the relative resistance of non actively proliferating cells versus their actively proliferating counterparts. The resistance of non actively proliferating cells to radiation treatment is only relative, however, as assessed by the inhibitory effect of radiation on endothelial cells, or the fibrosis or other side effects promoted by the radiotherapy.

Pure Gamma, pure Beta and mixed irradiations have been tested. Since the thickness of the arteries is in the mm range, Beta-irradiation is preferred over Gamma-irradiation in angioplasty-related applications, due to the known deeper effects of the latter (Waksman R. et al., 1995, Circulation 92:1383–1386). Obviously, Beta rays also present advantages concerning radioprotection. However, due to the limitations associated with the fixing of the isotope onto the support such as a stent (i.e. suitable isotopes, shelf life of the radioactive stent, production costs, etc.), the use of a Beta-isotope in such systems does not offer an optimal solution.

The question of half-life of the isotope used is of crucial importance from a practical, as well as from a biological point of view. It is generally understood that it is preferable to choose an isotope that would irradiate for the minimum during a time period sufficient to inhibit the proliferative activity of the targeted cells, thereby minimizing the irradiation of the surrounding tissues. It is known that in order for less than 1% of the total radioactivity of an isotope to remain requires the passing of 6 half-lives. However, the removal of the remaining 1% radioactivity will require a very long time if not an infinite amount of time. In the case of $^{32}P$ for example, which has a half-life of 14 days, 84 days are required to bring the level of radiation below the 1% mark. In the treatment of restenosis, for example, as radioactivity will mainly target smooth muscle cell proliferation, the need to be effective throughout the replication stage (approximately 15 days) has to be taken into consideration. Thus, a significant proportion of the radioactivity will remain in place long after the proliferation stage of the smooth muscle cells. It follows that the current technology is limited since the total radiation dose is controlled solely by the half-life and quantity of the chosen isotope.

It should be noted that all systems designed for delivering radioactivity to a targeted region have been based on implantation of the radioisotope to or beneath the surface of a support such as a stent. These systems aim at minimizing or even abrogating any "leeching" of the radioactivity from the support (Fischell et al., 1995, Circulation 92:1353–54). It should also be understood that, to date, no local radiation delivery system permits a flexible calculation and control of the total dose in the patient.

It would be beneficial for the medical and research practitioners to provide them with a radioactivity local delivery system that would be more practical to use, would limit unnecessary exposure to normal surrounding tissues, and could permit a more precise control of the dose and the dose rate of irradiation of the targeted cells.

SUMMARY OF THE INVENTION

In accordance with an aspect of the present invention, there is provided a method for determining a coefficient of diffusion of a radioisotope in a radioisotope-containing implant structure to administer to a vascular region of a patient's body a dose of radioactivity at a given dose rate, comprising:

calculating a relation between the coefficient of diffusion of the radioisotope in the implant structure and a coefficient of diffusion of the radioisotope in the vascular region of the patient's body for at least one given period of time during which the radioisotope has to be released from the implant structure; determining the diffusion coefficient of the vascular region; and determining, from the diffusion coefficient of the vascular region and in connection with the above mentioned relation, the diffusion coefficient of the implant structure required to release the radioisotope within the given period of time.

In accordance with preferred embodiments:
the method comprises introducing the radioisotope in a coating of the implant structure;
calculating a relation comprises calculating the relation between the coefficient of diffusion of the radioisotope in the implant structure and the coefficient of diffusion of the radioisotope in the vascular region both for the at least one given period of time and in connection with a given thickness of the coating;

calculating a relation comprises building a graph of this relation between the coefficient of diffusion of the radioisotope in the implant structure and the coefficient of diffusion of the radioisotope in the vascular region for said at least one given period of time;

calculating a relation comprises building many graphs of the relation between the coefficient of diffusion of the radioisotope in the implant structure and the coefficient of diffusion of the radioisotope in the vascular wall for said at least one given period of time, each graph being associated to a given thickness of this coating;

Another aspect of the present invention relates to a method for calculating a quantity of radioisotope to be introduced in an implant structure in view of administering to a vascular region of a patient's body a dose of radioactivity at a given dose rate, comprising: calculating a relation between a coefficient of diffusion of the radioisotope in the implant structure and a coefficient of diffusion of the radioisotope in the vascular region of the patient's body for at least one given period of time during which the radioisotope has to be released; determining the diffusion coefficient of the vascular region; determining, from the diffusion coefficient of the vascular region and in connection with the relation, the diffusion coefficient of the implant structure required to release the radioisotope within said given period of time; and calculating the quantity of radioisotope from the diffusion coefficient of the vascular region and the diffusion coefficient of the implant structure.

Preferably:

the implant structure is a stent having a plurality of struts for implantation in a blood vessel of the patient's body, and the method further comprises optimizing a spacing between pairs of adjacent struts in the direction of blood flow in a vascular wall of the blood vessel, this vascular wall constituting the vascular region; and the method further comprises combining the radioisotope with a chelating agent to form molecules, and introducing these molecules in the implant structure.

The present invention further relates to a helical stent to be implanted in a blood vessel of a patient's body, wherein the helical stent has a plurality of successive struts, contains a radioisotope, and has a given coefficient of diffusion of the radioisotope in the stent. The pairs of adjacent struts are separated by a spacing which increases in a direction of blood flow in a vascular wall of the blood vessel in order to make more uniform the distribution of the radioisotope in the vascular wall.

According to advantageous embodiments:

the helical stent comprises a coating containing the radioisotope, this coating being of predetermined thickness and having the given coefficient of diffusion of the radioisotope; and the coefficient of diffusion of the radioisotope is related to the coefficient of diffusion of the radioisotope in the vascular wall of the blood vessel.

The foregoing and other objects, advantages and features of the present invention will become more apparent upon reading of the following non-restrictive description of a preferred embodiment thereof, given by way of example only with reference to the accompanying drawings.

BRIEF DESCRIPTION OF THE DRAWINGS

In the appended drawings:

FIG. 4 is a partial cross sectional view showing the distribution of the radioisotope in the vascular wall of the blood vessel in which the helical stent of FIG. 2 has been placed;

FIG. 5 is a partial cross sectional view showing the distribution of the radioisotope in the vascular wall of the blood vessel in which a helical stent containing a fixed radioisotope has been placed;

DETAILED DESCRIPTION OF THE PREFERRED EMBODIMENT

The present invention therefore aims at controlling cell proliferation through local isotope irradiation. It should be understood, herein, that the present invention is not limited to a use in the reduction of coronary restinosis. Indeed, it is contemplated that the present invention can be used in a variety of clinical situations that include, without being limited thereto, cancer therapy, inhibition of keloide scares and treatment of heterotopic bone formation. The medical practitioner will be able to adapt the present invention to a particular clinical situation. For example, placement of a stent-like structure (stent implant, scaffolding structure, etc.) in a duct or track or even in bronche could locally deliver radiation, thereby inhibiting the proliferation of the targeted cells. It should be understood that the present invention can be adapted by a medical practitioner to enable modification of cancer radiotherapy of a chosen tissue or organ by the use of the present invention.

In the preferred embodiment as herein described, the present invention is aimed at controlling smooth muscle cells proliferation with a radioactive stent to reduce coronary restenosis after balloon angioplasty. Many arguments suggest the effectiveness of local radioactivity to reduce neointimal proliferation after balloon angioplasty. Coronary stents are increasingly used after angioplasty and indications will probably broaden in the future. The combination of both strategies in some clinical circumstances has previously been disclosed by the group of Fischell and others. However, these prior art methods rely on a stent rendered radioactive by activating the metal of the stent with particle bombardment (reactor, cyclotron). In that case, different radioisotopes emitting Gamma and Beta radiations with several energies and half-lives can be produced (Herlein C. et al., 1995, Circulation 92:1570–1575). It should be stressed that it remains to be determined whether the biocompatibility and hemocompatibility of the stent has been modified by this process of rendering it radioactive.

The present invention overcomes the drawbacks of the Fischell strategy by providing a radioactivity local delivery system which enables precise control of the total dose and dose rate of irradiation.

Figure 1:
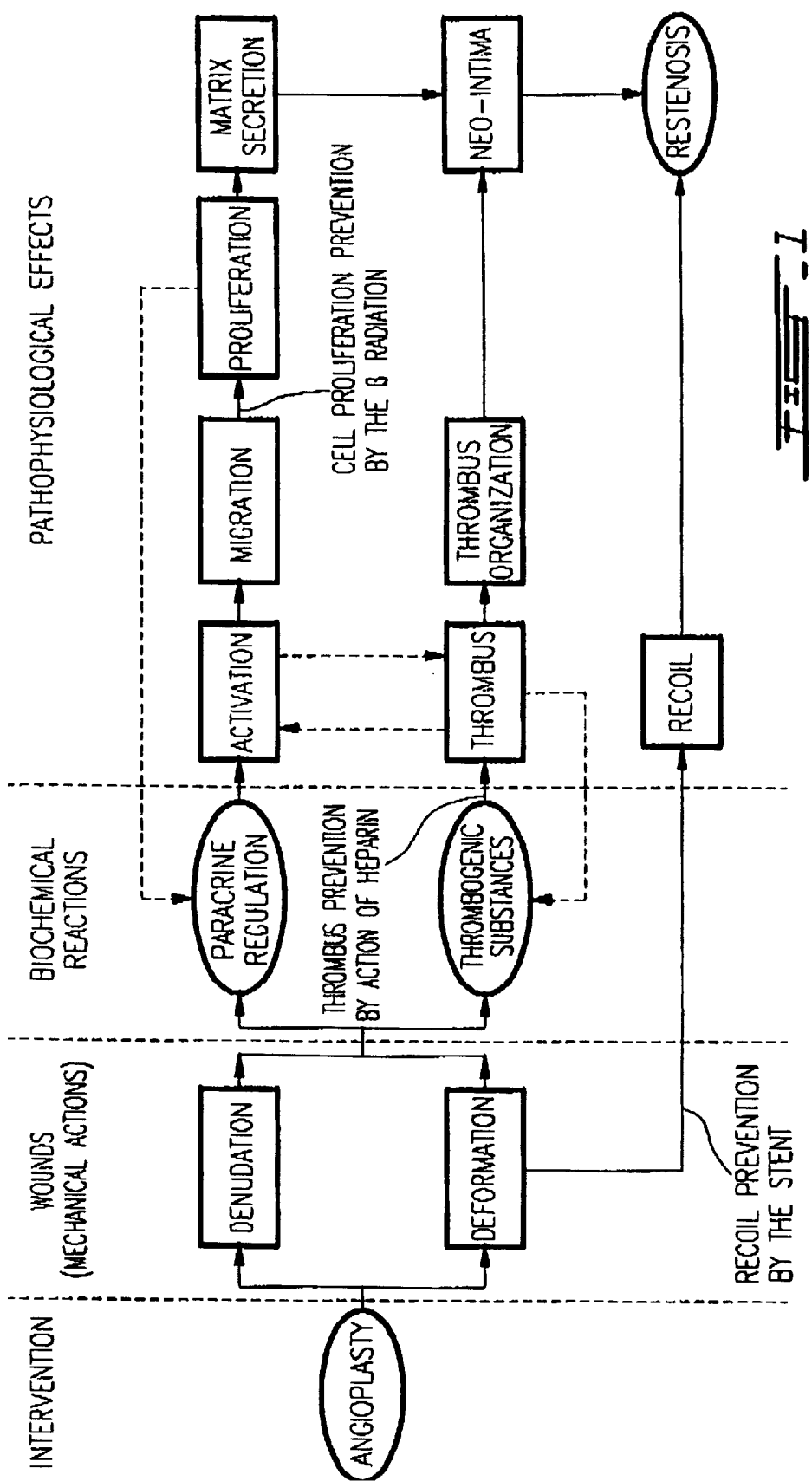
FIG. 1 is a schematic representation of a simplified model of the restenosis pathway.
Figure 2:
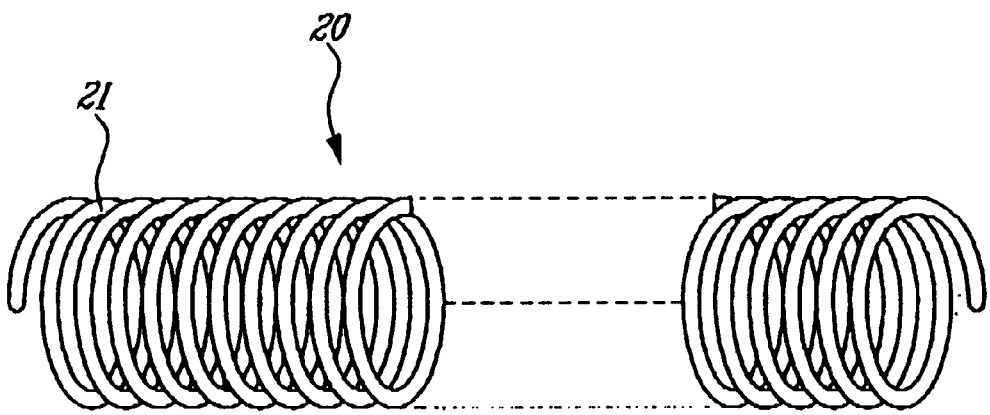
FIG. 2 is an elevation view of a helical stent according to the present invention.

In accordance with the preferred embodiment, a radioisotope is made available on the stent itself. Referring to FIG. 2, the stent 20 is formed of a helical wire 21 for being positioned, in particular but not exclusively, in a blood vessel such as an artery following angioplasty. In the present specification, the term "vessel" is used broadly to cover lumen, duct, and other types of bodily conduits. Wire 21 can be made of any suitable material such as biocompatible metals, polymers, plastics, etc.

Figure 3:
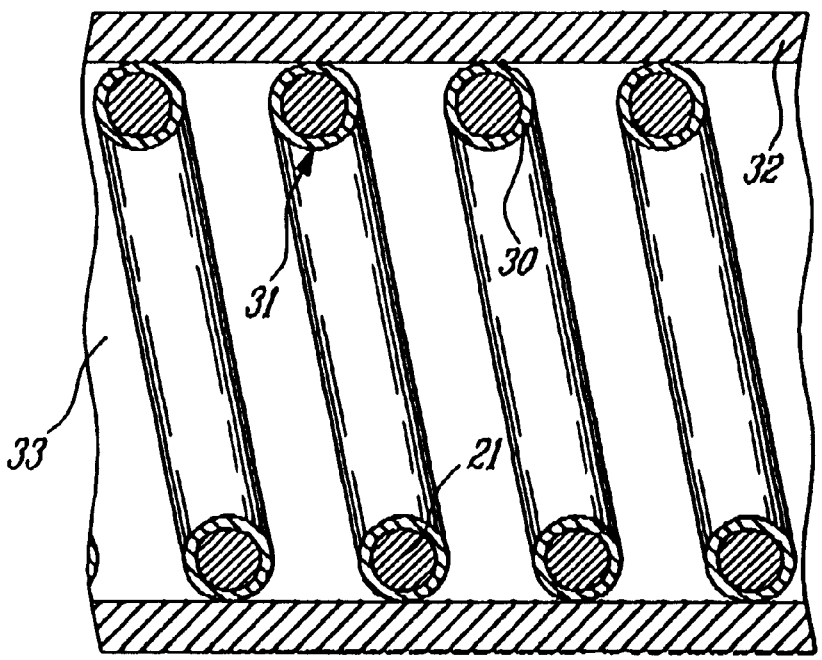
FIG. 3 is an enlarged cross sectional view of one strut of the helical stent of FIG. 2, showing a coating containing a radioisotope.

A suitable radioisotope is mixed with a carrier, for example a polymer. Referring to FIG. 3, a coating 30 of this polymer/radioisotope mixture is applied and bonded to the helical wire 21 of the stent 20. Just a word to mention that only one strut of the stent 20 is shown in FIG. 3.

The polymer of the coating 30 forms a radioisotope-retaining matrix and has a given coefficient of diffusion $D_p$ of the raidoisotope therein. This coefficient $D_p$ enables the radioisotope to diffuse through the polymer of the coating 30. The radioisotope is thereby eluted (released) at a given rate, dictated by this coefficient $D_p$ through the outer cylindrical surface 31 of the polymer coating 30.

Another alternative is to integrate the radioisotope inside a structure of polymer forming the stent itself. The polymer stent would then form a radioisotope-retaining matrix having a certain coefficient of diffusion $D_p$ of the isotope therein. This coefficient would enable the radioisotope to diffuse through the polymer stent. The radioisotope would be thereby released at a certain rate through the outer surface of the stent. In the case the polymer of the stent would be degradable, biodegradation of the polymer would play the dual role of releasing at a given rate the radioisotope and removing the stent itself. It is conceivable that in certain clinical situations, a stent could be withdrawn after a predetermined period of time.

Polymers which can be used as carriers for the purpose of the present invention include without being limited thereto natural biodegradable polymers such as fibrin, synthetic biodegradable polymers comprising polyglycolic acid/polylactic acid, polycaprolactone, polyhydroxybutyrate, polyorthoester, polyethyleneoxide/polybutylene terephtalate, and non biodegradable polymers such as polyurethane, silicone and polyethylene terephtalate. Of course, the use of mixtures of the above polymers, other polymers and any other suitable material could also be contemplated.

The radioisotope is coupled to an agent enabling rapid elimination thereof from the circulation of the living body, in particular but not exclusively the human body. Rapid elimination of the radioisotope minimizes the potential hazard of irradiation at sites distant from the region of local radiotherapy. Maximum complex stability is achieved via chelation. A chelate is formed when a metal atom is bound to more than one donor atom of a complexing molecule or ligand, thereby forming a closed-ring structure. The added stability of the metal chelate is often required in order to resist oxidation, hydrolysis or the strong affinity that some metals, especially indium and gallium, display for the plasma protein transfer. In general, metal-chelate complexes have characteristic physicochemical properties (i.e. molecular weight, lipid solubility, charge pKa proportion of protein binding, etc.), which will govern their in vivo distribution. It will be understood that the chelating agent will be chosen so as to promote the excretion of the radioisotope following leeching (release) from the polymer carrier.

The effects of radioactivity on the proliferation of cells makes radioactivity efficient in significantly reducing neointima formation following angioplasty and proliferation of actively proliferative cells such as for example tumor cells. Once again it will be understood that the medical practitioner can adapt the dose and dose rate to a treatment for cancer. Similarly, the type of radioisotope and carrier will be adapted to meet the requirements of the intended application.

Let's now examine an exemplary methodology to prescribe a precise radiation dose and dose rate in view of controlling endovascular restenosis using an eluting stent 20 according to the present invention.

A. Concentration Aspects:

In restenosis, smooth muscle cells proliferation occurs in a thin layer of about 400–800 $\mu$m of the inner vessel wall. Therefore, for this particular application, $\beta$-irradiation can be used. However, this should not be construed as eliminating the use of other types of irradiation. In the proposed model, the radioisotope is $^{45}$Ca and the chelating agent is DTPA (diethylene triaminepentaacetic acid) to form the molecule $^{45}$Ca-DTPA (hereinafter the molecule). Of course, it is within the scope of the present invention to use molecules other than $^{45}$Ca-DTPA; for example, the radioisotope could be $^{35}$S(sulfur) and the chelating agent EDTA (ethylene diaminetetraacetic acid).

In order to be able to determine a precise dose and dose rate, one must take into consideration the local pharmacokinetic of the molecule being eluted from the stent 20. This pharmacokinetic is strongly influenced by the blood flow, the diffusion properties in the vascular wall 32 of the blood vessel 33 (FIG. 3) and in the polymer coating 30 (thickness, size of the pores of the polymer material, etc.).

Dispersion of the molecule by the blood flow is characterized by the coupling of the Navier-Stokes equation $$\frac{\partial C}{\partial t} = \nabla \cdot \left(\frac{1}{Pe_w}\nabla C\right) \quad (1)$$

with the advection-diffusion equation:

$$\frac{\partial C}{\partial t} + (U \cdot \nabla)C = \nabla \cdot \left(\frac{1}{Pe_a}\nabla C\right) \quad (2)$$

where C is the concentration of the molecule in the polymer matrix or vascular wall, t represents time, $Pe_w$ is the Péclet number of the radioisotope in the vascular wall 32 of the blood vessel 33, where U is the speed of the blood, $Pe_a$ is the Péclet number of the radioisotope in the artery.

The distribution of the radioisotope in the vascular wall 32 is described as a purely diffusive process; more complex and realistic description with advection aspects can be achieved using porous models such as Darcy and Brinkman models. With this purely diffusive model and using the physical characteristics of $^{45}$Ca-DTPA molecules, the distribution of FIG. 4 is obtained in the vascular wall 32 and the vessel lumen 40.

Interestingly, FIG. 4, showing the concentration distribution of the radioisotope molecule, also shows that the eluting stent approach provides for non zero concentration of the molecule in the vascular wall 32 and vessel lumen 40 with a much more homogeneous distribution as compared to the approach where the isotope is fixed to the stent (FIG. 5).

Figure 6:
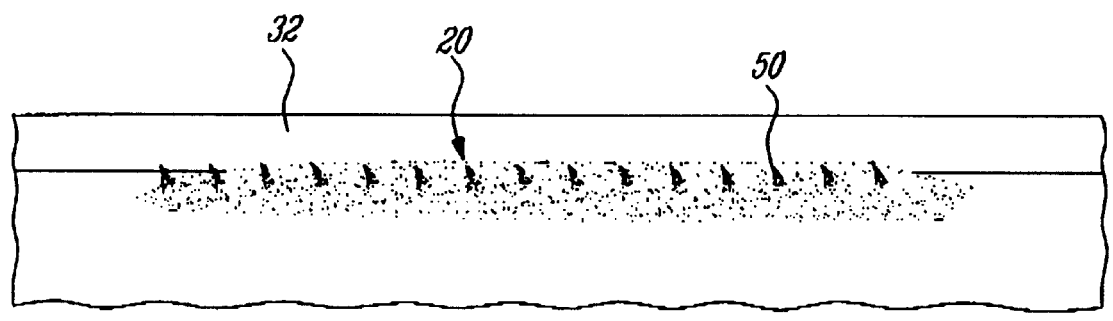
FIG. 6 is a partial cross sectional view showing a not completely uniform axial and longitudinal distributions of the radioisotope in the vascular wall of the blood vessel in which the helical stent of FIG. 2 has been placed.
Figure 7:
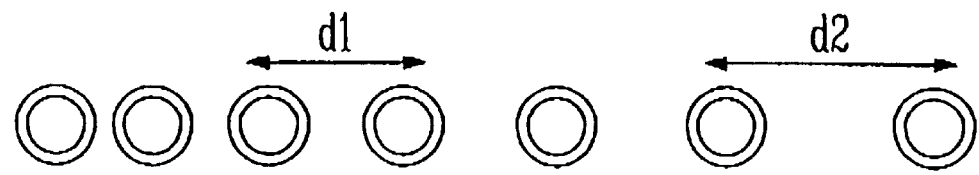
FIG. 7 is a partial cross sectional view showing a helical stent having struts spaced apart from each other by a distance which increases in the direction of the blood flow in the vascular wall of the blood vessel.

FIG. 6 shows the longitudinal distribution of the radioisotope molecule for fifteen adjacent struts such as 50 of the stent 20. From FIG. 6, it is noticed that the longitudinal and axial distributions of the molecule in the vascular wall 32 are not completely homogeneous with an even distance between the stent struts 50. Indeed, a downstream accumulation of the molecule is noticed. This brings the design proposal of asymmetric strut distribution of FIG. 7 to compensate for the bulk flow transport and rehomogenize the concentration of the molecule in the vascular wall 32. The uneven distances (see for example $d_1$ and $d_2$) are calculated to optimize the radioisotope distribution in the vascular wall 32. Distances may therefore vary according to properties of the radioisotope, the chelator and/or the polymer matrix formed by the coating 30.

A simple method to change the distance between struts would be to make the ratio of the concentrations in the vicinity of the strut equal according to:

$$d2/d1 = c2/c1 \text{ or } d2 = (c2/c1)*d1 \quad (3)$$

where c2 and c1 are the average concentrations over distance d2 and d1 respectively. This ratio should be kept constant for any pair of struts all along the stent.

B. Dosimetry Aspects

The radiation dose modeling is performed using a Point Kernel approach. The Loevinger type point kernel K(|r-r'|) is used, where K describes the dose rate at position r for a 1 Bq (where Bq signifies one Bequerel radiation unit) point source located at position r'. The total dose was calculated using a superposition of a point sources distribution:

$$D(\vec{r},t) = \int K(|\vec{r}-\vec{r}'|) a(\vec{r}',t) e^{-\lambda t} d_3 \vec{r}' \quad (4)$$

where $\lambda$ is the radioactive decay constant of the radioisotope and a is the activity at a given point in space r.

Using the Cross modified Loevinger kernel:

$$(vr)^2 K(r) = \begin{cases} k(C - vre^{1-vr/C} + vre^{1-vr} - vRe^{1-vR}), & \text{if } r < C/v \\ k(vre^{1-vr} - vRe^{1-vR}), & \text{if } C/v < r < R \\ 0 & \text{if } R > C/v \end{cases} \quad (5)$$

with $^{45}$Ca: $v = 144$ cm$^{-1}$, $C = 1.87$, $R = 49.9$ mg cm$^{-2}$, $k/v^2 = 141$ nGy cm$^2$ hr$^{-1}$.

Figure 8:
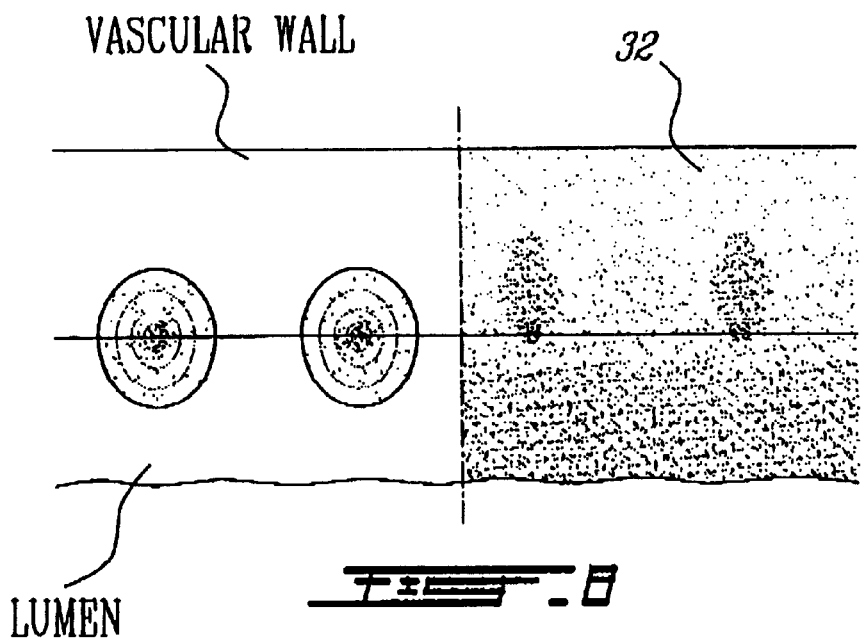
FIG. 8 is a partial cross sectional view showing, on the left, the radiation zone distribution when the radioisotope is fixed to the stent and, on the right, the radiation dose distribution when the radioisotope is eluted (released) from the stent.

FIG. 8 shows a comparison of concentration distributions and dose computations between eluting and non eluting radioactive $^{45}$Ca-DTPA stent designs. The left side of FIG. 8 illustrates the radiation dose distribution for the case where the radioisotope is fixed to the stent. The right side of FIG. 8 represents the radiation dose distribution where the radioisotope is eluted from the stent 20. FIG. 8 clearly shows the advance of the eluting radioisotope stent approach regarding homogeneity of irradiation of the vascular wall 32.

In the following description, a methodology is developed for quantifying the precise dose and dose rate in order to ensure an optimal and efficient therapeutic effect. In the prior art, only the initial radioactivity put on the stent 20 is given (with the above model this corresponds to variable C). The dose is rarely, and the dose rate even more rarely mentioned and when it is mentioned there is never a description of a method to derive an optimal and efficient dose and dose rate. Instead, in the present invention, the activity that has to be put on the stent is calculated from the total dose and dose rate the physician wants to deliver to the target tissue, i.e. the vascular wall 32.

In order to calculate an initial activity that will provide the required effective radiation dose and dose rate, it is necessary to first combine the radioactive decay on the molecule (radioisotope) with the advection-diffusion aspects. However, to avoid the problems of storage associated with the intensive computations (every velocities, pressure, shear, concentrations at every time step), the system of equations resulting from the time average of the concentration of the molecule in the vascular wall 32 in time is solved:

$$q(\vec{x}) = \int_0^\infty C(\vec{x},t) e^{-\lambda t} dt \quad (6)$$

where C is the concentration of the molecule in the polymer matrix, q the time average of this concentration (or total activity), and $\lambda$ the radioactive decay constant of the radioisotope at a given point in space x. The value q, is interpreted as the total accumulation over time of the molecule at a given point of the vascular wall 32.

The advection-diffusion equation is also integrated (average in time). In a first step, this advection-diffusion equation is multiplied by the radioactive decay:

$$e^{-\lambda t}\frac{\partial C}{\partial t} + e^{-\lambda t}(U \cdot \nabla)C = \frac{e^{-\lambda t}}{Pe}\nabla^2 C$$

where Pe is the Péclet number of the radioisotope. After rearranging and integration, the following equation is obtained:

$$-C_0 + \lambda q + (U \cdot \nabla)q = \frac{1}{Pe_b}\nabla^2 q$$

Where $Pe_b$ is the Péclet number of the radioisotope in the blood.

Using the same procedure, the following equations are obtained for the polymer and the vascular wall, respectively.

$$-C_0 + \lambda q + (U \cdot \nabla)q = \frac{1}{Pe_p} \nabla^2 q \qquad (9)$$

$$-C_0 + \lambda q + (U \cdot \nabla)q = \frac{1}{Pe_w} \nabla^2 q \qquad (10)$$

where $Pe_p$ and $Pe_w$ are the Péclet number of the radioisotope into the polymer and vascular wall, respectively. The value of $\lambda$ for $^{45}$Ca-DTPA is $1.043705 \times 10^{-10}$.

The above set of equations (6) to (10) is one core result of the proposed exemplary methodology to determine a precise and efficient dose and dose rate. In contrast with the prior art, the average dose rate (the amount of dose by unit of time) is determined as a critical requirement to control local cell proliferation. In order to control the restenosis process, it is not only the total dose that matters but also the dose rate. If the dose rate is too low whatever the total dose, cell proliferation will compensate for cell killing.

Figure 9:
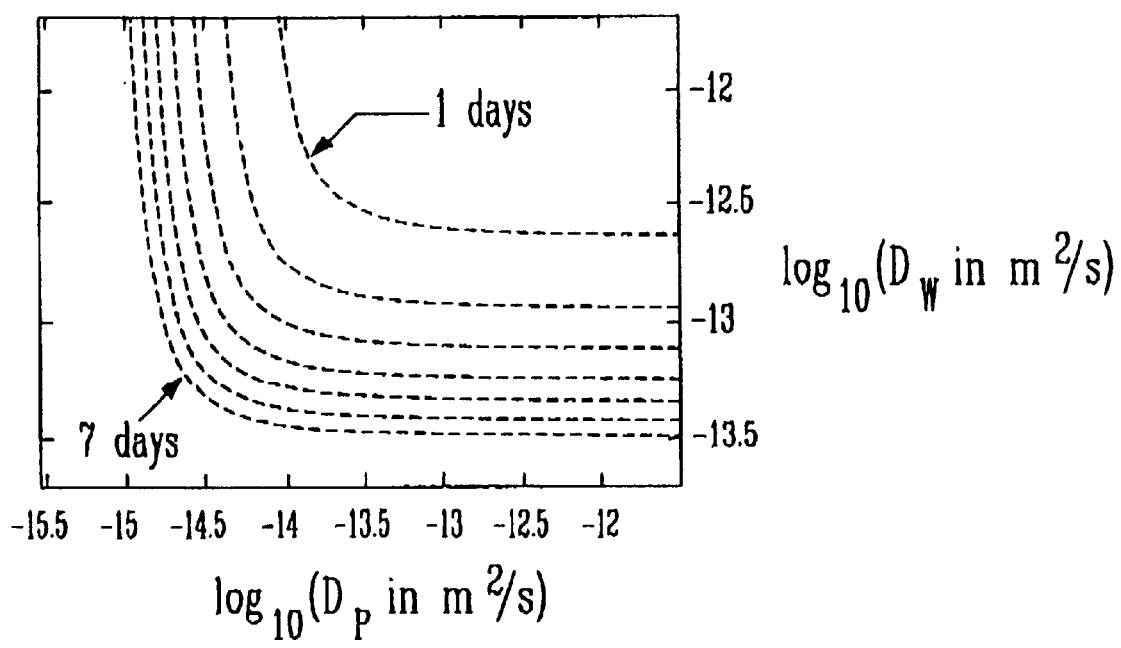
FIG. 9 is a first chart of the logarithm of the coefficient of diffusion $D_p$ of the radioisotope in the polymer material of the coating of the stent with respect to the logarithm of the coefficient of diffusion $D_w$ of the radioisotope in the vascular wall of the blood vessel, for various periods of time during which the radioisotope has to be substantially totally released from the coating and for a coating 25 $\mu$m thick.
Figure 10:
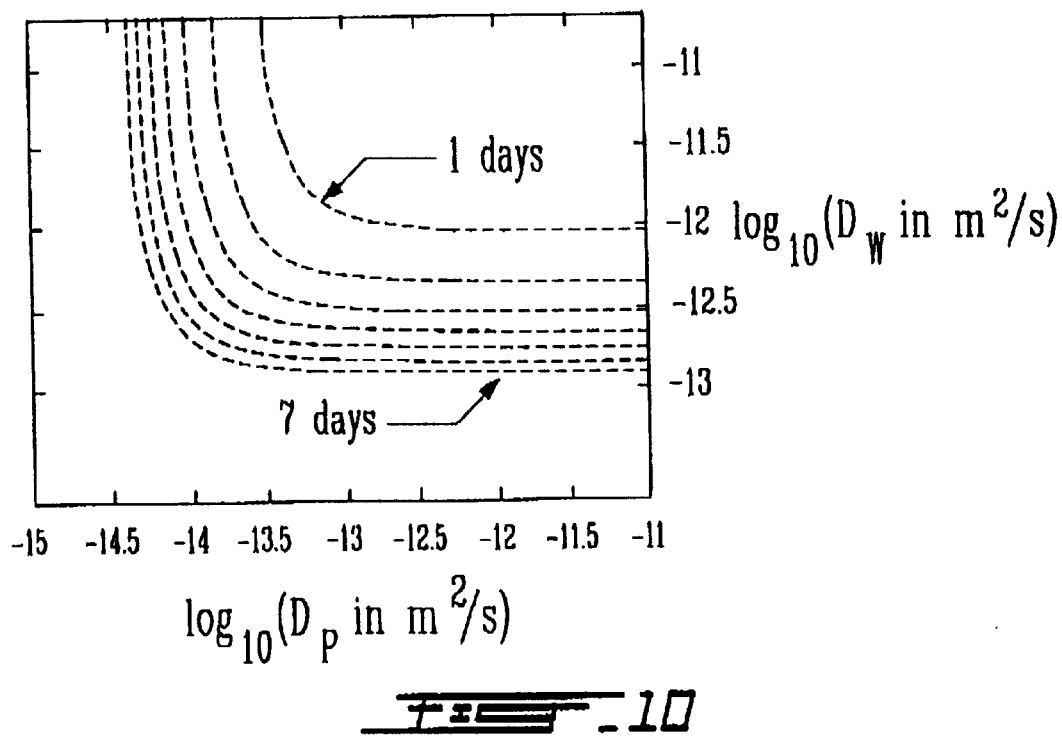
FIG. 10 is a second chart of the logarithm of the coefficient of diffusion $D_p$ of the radioisotope in the polymer material of the coating of the stent with respect to the logarithm of the coefficient of diffusion $D_w$ of the radioisotope in the vascular wall of the blood vessel, for various periods of time during which the radioisotope has to be substantially totally released from the coating and for a coating 50 $\mu$m thick.
Figure 11:
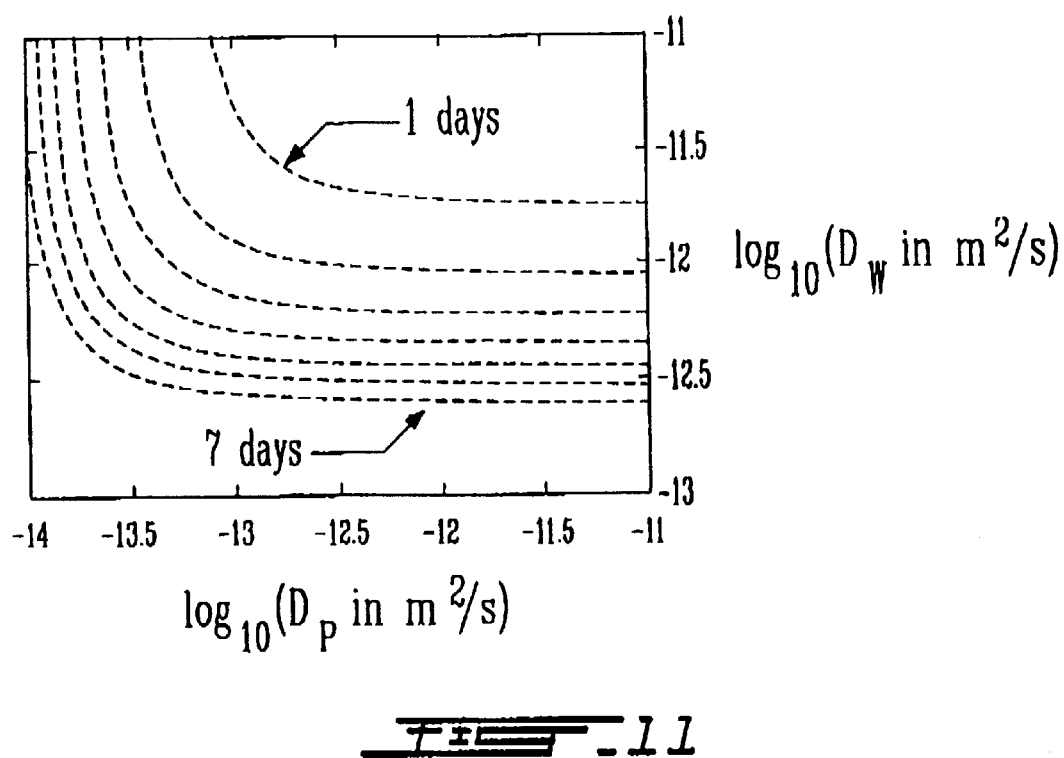
FIG. 11 is a third chart of the logarithm of the coefficient of diffusion $D_p$ of the radioisotope in the polymer material of the coating of the stent with respect to the logarithm of the coefficient of diffusion $D_w$ of the radioisotope in the vascular wall of the blood vessel, for various periods of time during which the radioisotope has to be substantially totally released from the coating and for a coating 75 $\mu$m thick.
Figure 12:
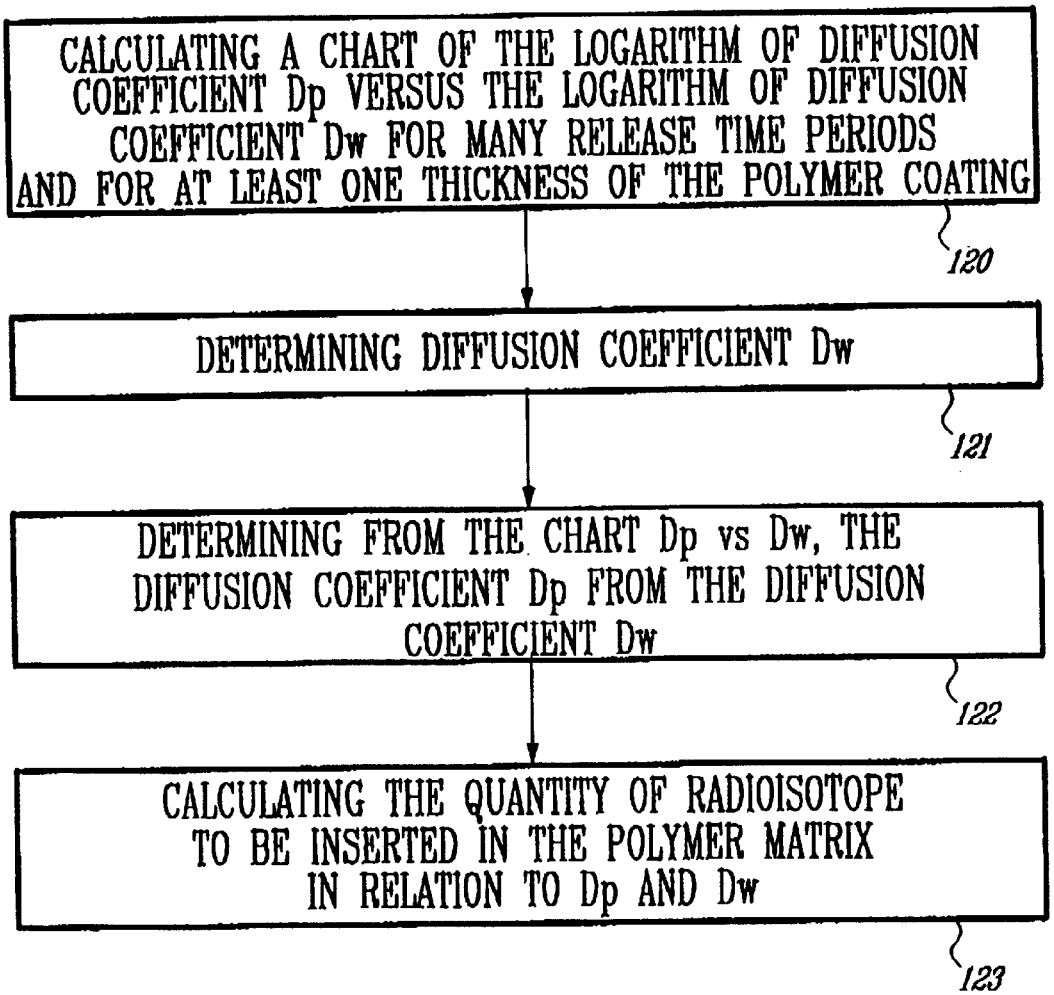
FIG. 12 is a flow chart showing the different operations conducted by the above described methods according to the present invention.

The above set of equations (6) to (10) is solved for several polymer coating thickness as well as for a range of Péclet numbers of the polymers to account for the different types of polymers. All the solutions can be visualized by constructing chart curves as shown in FIGS. 9, 10 and 11 (see block 120 of FIG. 12). The curve of the chart of FIG. 9 corresponds to a polymer coating thickness of 25 µm. The curve of the chart of FIG. 10 corresponds to a polymer coating having a thickness of 50 µm. Finally, the curve of the chart of FIG. 11 is related to a polymer coating thickness of 75 µm.

These charts are very useful tools for the proposed methodology to determine the precise dose and dose rate. In the following, the method of using these charts is described.

We will now refer more particularly of the chart of FIG. 11, which corresponds to a coating 30 of polymer having a thickness of 75 µm. In principle, the diffusion coefficient of the molecule is known, or can be measured for a given polymer compound. For example, if the diffusion coefficient DP in the polymer coating has a value is $10^{-13}$ m$^2$/s, a vertical is traced at $-13$ on the logarithmic scale (horizontal axis). Depending on the diffusion coefficient $D_w$ in the vascular wall 32, the chart indicates at what rate the substance is being eluted. For example, when the diffusion coefficient $D_w$ of the molecule in the vascular wall 32 is about $10^{-12.6}$ m$^2$/s the substance would be released in 7 days, with an emptying being defined as 90% of the original amount of the molecule in the polymer coating 30. However, if the diffusion coefficient $D_w$ of the molecule in the vascular wall 32 had a value of about $10^{-11.6}$ m$^2$/s, the molecule would then be released in only 1 day.

The above exemplary methodology is therefore capable of determining the initial amount of radioactivity, or quantity of molecules $^{45}$Ca-DTPA to put in the coating 30 of the stent 20 suitable to administer a given dose and dose rate. Furthermore, the presently described methodology proposes to define an effective therapeutic window based on 60 Gy in 7 days equivalent. Of course it is within the scope of the present invention to implement time periods other than 7 days and radioactivity levels other than 60 Gy. This simply means that when the treatment is protracted and given over a certain period of time, the therapeutic effect of these fractionations are equivalent according to the 60 Gy in 7 days equivalent curve. As indicated in the foregoing description, a given dose given at a lower dose rate will have a lower biological effect (killing effect). If the dose rate is too low whatever the total dose, cell proliferation will compensate for cell killing. Said differently, this means that using a lower dose rate will require a higher total dose to maintain the same biological effect. Calculation of the total dose and dose rate are therefore intrically linked.

According to the present exemplary approach, a treatment over 7 days is preferred. This means that in the charts of FIGS. 9–11, we move along the 7-day release curve. In practice the diffusion coefficient $D_w$ in the vascular wall 32 will be determined by the physiology of the artery and we have no control over it (block 121 of FIG. 12). However, given this diffusion coefficient $D_w$, the 7-day curve of the charts of FIGS. 9–11 can be used to determine the required diffusion coefficient $D_p$ of the molecule into the polymer of the coating 30 in order to obtain a 7-day release (block 122 of FIG. 12). The polymer can then be tailored in order to obtain the desired diffusion coefficient $D_p$.

Given the diffusion coefficients $D_w$ and $D_p$, those of ordinary skill in the art will appreciate that it is then possible to calculate the precise initial quantity of radioisotope necessary for administering the required dose and dose rate for the desired therapeutic effect within a prescribed period of time. The use of a digital model simulating blood flow conditions and diffusion-advection of the radioisotope is a helpful approach to determine the initial activity to incorporate into the polymer matrix of the coating 30.

The proposed procedure to calculate the precise initial quantity of radioisotope necessary for administering the required dose and dose-rate is to first compute the effective concentration distribution q(x) according to equations (8)–(10) (which take into account the half life the isotope). Then from this value q(x), the activity a (see equation (4)) is determined using the specific activity of the given isotope. From the activity a, the dose D (see equation (4)) is calculated from which finally the dose rate can be computed.

In conclusion, the above described methodology enables the design of a radioisotope eluting stent incorporating the precise initial quantity of radioisotope necessary for administering the required dose and dose rate. And this stent will integrate the complex relationships between the radiobiology of continuous low dose rate, the local blood flow mechanics, the diffusion-advection principles and the polymer-coated stent design.

Just a word to mention that, in the present disclosure and the appended claims, the term "patient" is intended to designate human being and animals other than human beings as well.

Although the present invention has been described hereinabove by way of a preferred embodiment thereof, this embodiment can be modified at will, within the scope of the appended claims, without departing from the spirit and nature of the subject invention.

What is claimed is:

1. A method for determining a coefficient of diffusion of a radioisotope in a radioisotope-containing implant structure to administer to a vascular region of a patient's body a dose of radioactivity at a given dose rate, comprising:
    calculating a relation between the coefficient of diffusion of the radioisotope in the implant structure and a coefficient of diffusion of the radioisotope in the vascular region of the patient's body for at least one given period of time during which the radioisotope has to be released from said implant structure;
    determining the diffusion coefficient of the vascular region; and
    determining, from the diffusion coefficient of the vascular region and in connection with said relation, the diffusion coefficient of the implant structure required to release the radioisotope within said given period of time.

2. A method as defined in claim 1, comprising introducing the radioisotope in a coating of said implant structure.

3. A method as defined in claim 1, wherein calculating a relation comprises calculating said relation between the coefficient of diffusion of the radioisotope in the implant structure and the coefficient of diffusion of the radioisotope in the vascular region both for said at least one given period of time and in connection with a given thickness of the coating.

4. A method as defined in claim 1, wherein calculating a relation comprises building a graph of said relation between the coefficient of diffusion of the radioisotope in the implant structure and the coefficient of diffusion of the radioisotope in the vascular region for said at least one given period of time.

5. A method as defined in claim 1, wherein calculating a relation comprises building many graphs of said relation between the coefficient of diffusion of the radioisotope in the implant structure and the coefficient of diffusion of the radioisotope in the vascular wall for said at least one given period of time, each graph being associated to a given thickness of said coating.

6. A method for calculating a quantity of radioisotope to be introduced in an implant structure in view of administering to a vascular region of a patient's body a dose of radioactivity at a given dose rate, comprising:

calculating a relation between a coefficient of diffusion of the radioisotope in the implant structure and a coefficient of diffusion of the radioisotope in the vascular region of the patient's body for at least one given period of time during which the radioisotope has to be released;

determining the diffusion coefficient of the vascular region;

determining, from the diffusion coefficient of the vascular region and in connection with said relation, the diffusion coefficient of the implant structure required to release the radioisotope within said given period of time; and calculating said quantity of radioisotope from the diffusion coefficient of the vascular region and the diffusion coefficient of the implant structure.

7. A method as recited in claim 6, comprising introducing the radioisotope in a coating of said implant structure.

8. A method as recited in claim 6, wherein calculating a relation comprises calculating said relation between the coefficient of diffusion of the radioisotope in the implant structure and the coefficient of diffusion of the radioisotope in the vascular region both for said at least one given period of time and in connection with a given thickness of the coating.

9. A method as recited in claim 6, wherein calculating a relation comprises building a graph of said relation between the coefficient of diffusion of the radioisotope in the implant structure and the coefficient of diffusion of the radioisotope in the vascular region for said at least one given period of time.

10. A method as recited in claim 6, wherein calculating a relation comprises building many graphs of said relation between the coefficient of diffusion of the radioisotope in the implant structure and the coefficient of diffusion of the radioisotope in the vascular wall for said at least one given period of time, each graph being associated to a given thickness of said coating.

11. A method as recited in claim 6, wherein said implant structure is a helical stent having a plurality of struts for implantation in a blood vessel of the patient's body, and wherein said method further comprises optimizing a spacing between pairs of adjacent struts in the direction of blood flow in a vascular wall of the blood vessel, said vascular wall constituting said vascular region.

12. A method as recited in claim 6, further comprising combining the radioisotope with a chelating agent to form molecules, and introducing said molecules in the implant structure.

* * * * *